United States Patent [19]

Joshi et al.

[11] Patent Number: 4,808,413

[45] Date of Patent: Feb. 28, 1989

[54] PHARMACEUTICAL COMPOSITIONS IN THE FORM OF BEADLETS AND METHOD

[75] Inventors: Yatindra M. Joshi, Piscataway; William R. Bachman, North Brunswick; Nemichand B. Jain, Monmouth Junction, all of N.J.

[73] Assignee: E. R. Squibb & Sons, Inc., Princeton, N.J.

[21] Appl. No.: 140,281

[22] Filed: Dec. 31, 1987

Related U.S. Application Data

[63] Continuation-in-part of Ser. No. 43,584, Apr. 28, 1987, abandoned.

[51] Int. Cl.$^4$ .......................... A61K 9/14; A61K 9/26; A61K 9/52
[52] U.S. Cl. .................................... 424/458; 424/469; 424/489
[58] Field of Search ....................... 424/489, 493–495, 424/458, 469

[56] References Cited

FOREIGN PATENT DOCUMENTS 0122077  3/1984  European Pat. Off. .
123470A  4/1984  European Pat. Off. .
6136217  6/1984  Japan .

Primary Examiner—Michael Lusignan
Attorney, Agent, or Firm—Lawrence S. Levinson; Burton Rodney

[57] ABSTRACT

A pharmaceutical composition is provided which is in the form of a plurality of beadlets, adapted to be filled into pharmaceutical hard shell capsules, or compressed into tablets, which beadlets are formed of a pharmaceutical such as an ACE inhibitor, for example, captopril, a beta-blocker such as nadolol, propranolol or atenolol, a calcium channel blocker such as diltiazem or nifedipine or other pharmaceuticals including combinations thereof, binder such as microcrystalline cellulose, and at least 5% by weight of an acid processing aid, such as citric acid, which imparts plasticity to the wet mass needed for efficient extrusion and spheronization. A method for forming beadlets is also provided which includes the steps of extruding a composition as described above, and subjecting the resulting extrudate to a spheronization step wherein an acid processing aid such as citric acid is employed to improve processing and form improved beadlets.

35 Claims, No Drawings

PHARMACEUTICAL COMPOSITIONS IN THE FORM OF BEADLETS AND METHOD

REFERENCE TO OTHER APPLICATIONS

This application is a continuation-in-part of application Ser. No. 43,584, filed Apr. 28, 1987, now abandoned.

FIELD OF THE INVENTION

The present invention relates to a new pharmaceutical composition in the form of beadlets which contain one or more pharmaceuticals, such as an ACE inhibitor, beta blocker, calcium channel blocker or combinations thereof and at least 5% by weight of an organic acid such as citric acid, and to a method for forming such beadlets.

BACKGROUND OF THE INVENTION

U.S. Pat. No. 4,105,776 to Ondetti et al discloses proline derivatives which are angiotensin converting enzyme (ACE) inhibitors and have the general formula

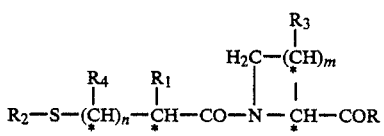

which includes captopril

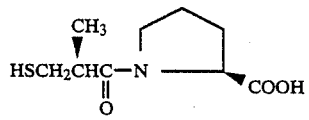

U.S. Pat. No. 4,168,267 to Petrillo discloses phosphinylalkanoyl prolines which have the formula

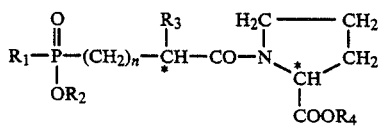

wherein
 $R_1$ is lower alkyl, phenyl or phenyl-lower alkyl;
 $R_2$ is hydrogen, phenyl-lower alkyl or a metal ion;
 $R_3$ is hydrogen or lower alkyl;
 $R_4$ is hydrogen, lower alkyl, phenyl-lower alkyl or a metal ion; and
 n is 0 or 1.

U.S. Pat. No. 4,337,201 to Petrillo discloses phosphinylalkanoyl substituted prolines having the formula

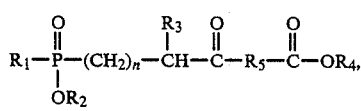

or a salt thereof, which covers fosinopril

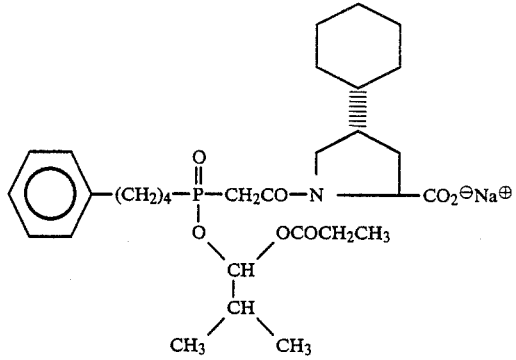

U.S. Pat. No. 4,432,971 to Karanewsky et al discloses phosphonamidate substituted amino or imino acids which are angiotensin converting enzyme inhibitors and salts thereof and have the formula

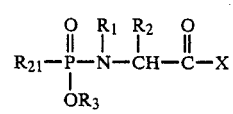

which includes 1-[N-[hydroxy(4-phenylbutyl)-phosphinyl]-L-alanyl]-L-proline, dilithium salt

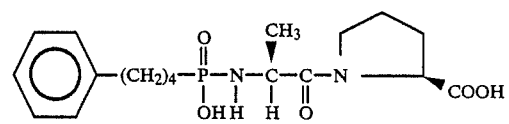

and 1-[N²-[hydroxy(4-phenylbutyl)phosphinyl]-L-lysyl]-L-proline, dilithium salt

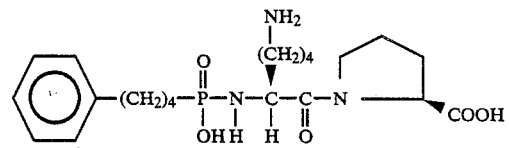

U.S. Pat. No. 4,374,829 to Patchett et al discloses carboxylakyl dipepetide derivatives which are said to be angiotensin converting enzyme inhibitors and have the formula

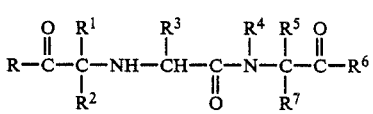

which covers enalapril

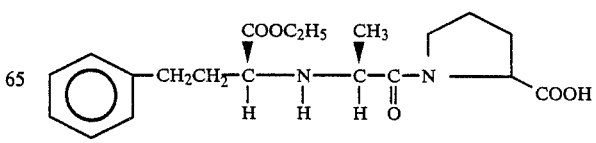

that is, N-(1-ethoxycarbonyl-3-phenylpropyl)-L-alanyl-L-proline.

U.S. Pat. No. 4,452,790 to Karanewsky et al is directed to phsophonate substituted amino or imino acids and salts thereof having the formula

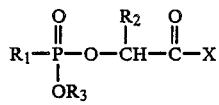

which covers SQ29,852

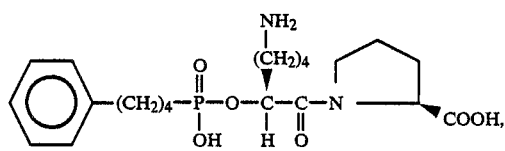

that is, (S)-1-[6-amino-2[[-hydroxy(4-phenylbutyl)phosphinyl]oxy]-1-oxohexyl]-L-proline.

U.S. Pat. No. 4,248,883 to Sawayame et al discloses 1-(3-mercapto-2-methylpropanoyl)prolyl amino acid derivatives of the formula

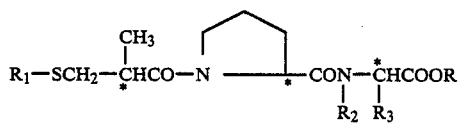

wherein

R represents a hydrogen atom, a lower alkyl group, a phenylo-lower alkyl group or a substituted phenyl-lower alkyl group; $R_1$ represents a hydrogen atom, $R_4CO—$, $R_5S—$ or

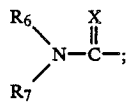

$R_2$ represents a hydrogen atom or a lower alkyl group;

$R_3$ represents a hydrogen atom, a phenyl group, a lower alkyl group, or a substituted lower alkyl group in which the substituent is hydroxy, phenyl-lower alkoxy, amino, guanidino, N-nitroguanidino, carboxyl, lower alkoxycarbonyl, phenyl-lower alkoxycarbonyl, carbamoyl, mercapto, lower alkylthio, phenyl, hydroxyphenyl, indolyl or imidazolyl; or $R_2$ and $R_3$ form a heterocyclic ring together with the nitrogen and carbon atoms to which they are respectively bonded; $R_4$ represents a lower alkyl group, a lower alkoxy group, a phenyl group, a substituted phenyl group, a phenyl-lower alkyl group, a substituted phenyl-lower alkyl group, a phenyl-lower alkoxy group, a substituted phenyl-lower alkoxy group, a phenoxy group, or a substituted phenoxy group; $R_5$ represents a lower alkyl group, a phenyl group, a substituted phenyl group, a phenyl-lower alkyl group, a substituted phenyl-lower alkyl group,

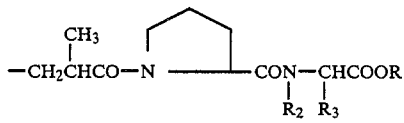

or an amino(-carboxy)lower alkyl group; $R_6$ represents a hydrogen atom or a lower alkyl group; $R_7$ represents a lower alkyl group, a phenyl group or a substituted phenyl group; X represents an oxygen or sulfur atom; and the substituent in the substituted phenyl group is a halogen atom, a lower alkyl group, or a lower alkoxy group; and salts of said derivatives.

U.S. Pat. No. 4,316,906 to Ondetti et al discloseds ether and thioether mercaptoacyl prolines of the formula

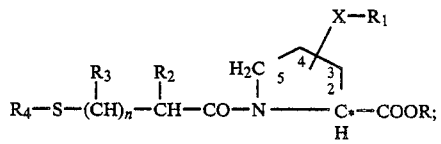

which includes zofenopril

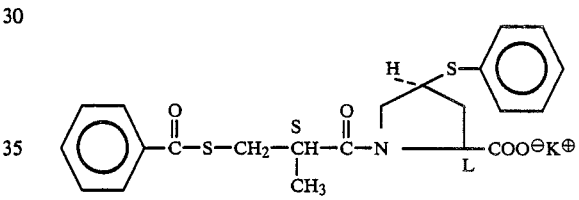

Japanese Laid-Open Patent Application (kokai) No. 61-36217 discloses sustained-release ACE inhibitor formulations wherein the ACE inhibitor is suspended in a lipophilic (oil or fat) base together with one or more of ascorbic acid, sodium ascorbate, erythorbic, acid, sodium erythorbate, sodium hydrogen sulfite, sodium sulfite and metabisulfite, and a viscosity enhaner such as hydroxypropylmethyl cellulose or methyl cellulose. The lipophilic base is present in a weight ratio to the ACE inhibitor of from about 3:1 to about 12:1.

U.S. Pat. No. 3,365,365 to Butler et al discloses pharmaceutical compositions in the form of beadlets capable of being embodied in hard shell capsules. In one embodiment, beadlets contain and furnish two separate and distinct doses of medicament which is accomplished in part by an enteric coating containing zein and an abietic acid type resin. In a second embodiment, beadlets contain and permit an active medicament to be released in a continuous fashion which is accomplished by a series of layers including an adhesive gum acacia layer into which an active inhgredient is dispersed, and a permeable film of shellac and polyethylene glycol 4000 to 20,000 overlaying the medicament-coated layer.

European Patent Application No. 0122077 (Elan) discloses prolonged release theophylline multilayer granules or pellets formed of theophylline (3.59 g), organic acid, such as citric acid (875 g) and soluble polymer with an outer membrane of poorly soluble polymer.

European Pat. No. 123470A discloses sustained release propranolol which is formed of alternate layers of propranolol, organic acid and mainly water-soluble polymer with a less soluble outer membrane. Granules for oral administration include a nucleus of propranolol (1000 g) or its acceptable salt and an organic acid such as citric acid (500 g) embedded in a polymer material in a multiple layer arrangement with an external membrane.

DESCRIPTION OF THE INVENTION

In accordance with the present invention, a new pharmaceutical composition is provided which acts as a controlled release formulation in the form of beadlets of medicament, for example, ACE inhibitor, such as captopril, zofenopril or fosinopril, beta-blocker, such as nadolol, propranolol or atenolol, calcium channel blocker such as diltiazem or nifedipine, or any of the pharmaceuticals as set out hereinafter or combinations thereof, capable of being filled into pharmaceutical hard shell capsules or compressed into a tablet. The new pharmaceutical composition of the invention is an excellent controlled release mechanism for release of pharmaceutical in the stomach and/or upper intestines for up to a 12 hour period and which appears to be at least bioequivalent to the presently available tablets of the same medication.

The beadlets forming the controlled release formulation of the invention are each formed of the medicament, a non-lipophilic binder-excipient, and an organic carboxylic acid, such as citric acid and which will be employed in amounts to provide at least about 5% by weight and preferably at least about 10% by weight of organic acid based on the total weight of the formulation. The beadlets may also optionally include one or more auxillary binders, one or more fillers or excipients, one or more lubricants, water and/or other conventional additives. However, the beadlets must include the above weight percent of organic acid as described hereinbefore, regardless of the other components present for the reasons as will be set forth hereinafter.

The beadlet of the invention formed of the above ingredients may be uncoated or may be a core coated with an acceptable pharmaceutical coating which will include from about 60 to about 95% by weight of one or more film formers, from about 5 to about 40% by weight of one or more plasticizers, one or more solvents and/or other conventional ingredients, the above % being based on the total weight of the coating.

In addition, in accordance with the present invention, a method is provided for preparing beadlets, such as described above, which method includes the steps of mixing the medicament, for example, ACE inhibitor, with binder-excipient and organic acid in water or an organic solvent to form a wet mass, extruding the wet mass to form an extrudate and spheronizing the extrudate to form beadlets. The beadlets may then be dried and optionally coated as described above.

It surprisingly has been found that the presence of large amounts of organic carboxylic acid, for example, citric acid, such as at least about 5% by weight and preferably at least about 10% by weight of the final beadlet, facilitates processing by imparting needed plasticity to the wet mass required for efficient and high quality extrusion and spheronization, reducing water requirements and shortening processing time, and aids in the formation of very hard beadlets, that is, a hardness of from about 2 to about 5 as measured by Strong-Cobb Units as compared to the for comparable size non-pareil beads. The friability of the resulting beads is extremely low, that is, less than 0.03% versus 6 to 7% for non-pareil beads. In addition, due to the presence of the organic acid, the beadlets are not ground up during the spheronization step so that desired narrow particle size distribution of from about 0.8 to about 2 mm diameter is obtained.

The beadlets of the invention will contain from about 3 to about 60% by weight medicament and preferably from about 6 to about 50% by weight medicament. The preferred medicament for use herein is an angiotensin converting enzyme inhibitor or a calcium channel blocker or combinations thereof.

The angiotensin converting enzyme inhibitor which may be employed herein includes substituted proline derivatives, such as any of those disclosed in U.S. Pat. No. 4,105,776 to Ondetti et al mentioned above, with captopril, that is, 1-[(2S)-3-mercapto-2-methylpropionyl]-L-proline, being preferred, carboxyalkyl dipeptide derivatives, such as any of those disclosed in European Patent Application No. 012 401 mentioned above, with N-(1-ethoxycarbonyl-3-phenylpropyl)-L-alanyl-L-proline, that is, enalapril, being preferred.

Other examples of angiotensin converting enzyme inhibitors suitable for use herein include any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline being preferred, phosphinylalkanoyl prolines disclosed in U.S. Pat. No. 4,168,267 mentioned above with fosinopril being preferred, mercaptoacyl derivatives of substituted prolines with zofenopril being preferred, any of the phosphinylalkanoyl substituted prolines disclosed in U.S. Pat. No. 4,337,201 discussed above, and the phosphonamidates disclosed in U.S. Pat. No. 4,432,971 discussed above.

Other examples of ACE inhibitors that may be employed herein include Beecham's BRL 36,378 as disclosed in European Pat. Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Pat. No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Pat. No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); R₀ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Beta-blockers which may be employed herein include nadolol, propranol, atenolol, timolol, metoprolol tartrate, acebutolol HCl, pindolol and the like.

Examples of calcium channel blockers or calcium antagonists suitable for use herein include diltiazem, as well as other calcium antagonists disclosed in U.S. Pat. No. 3,562,257, verapamil, tiapamil, 4-phenyl-1,4dihydropyridines as defined hereinafter (including nifedipine) and the like.

4-Phenyl-1,4-dihydropyridine calcium antagonists which may be employed herein have the structure

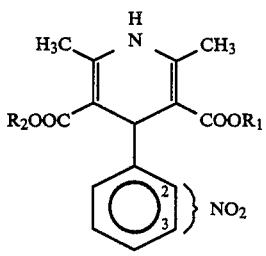

A.

wherein R₁ and R₂ may be the same or different and are lower alkyl or lower alkoxy (lower alkyl) where lower alkyl and lower alkoxy contain 1 to 4 carbons.

The above compounds and methods for preparing same are disclosed in U.S. Pat. Nos. 3,644,627, 3,485,847, 3,488,359, 3,574,843, 3,799,934, 3,932,645 and 4,154,839 which are incorporated herein by reference.

The dihydropyridine calcium antagonist present in the beadlet composition of the invention will preferably be nifedipine, that is, the compound of formula A wherein R₁ is CH₃, R₂ is CH₃ and NO₂ is at the 2-position, namely,

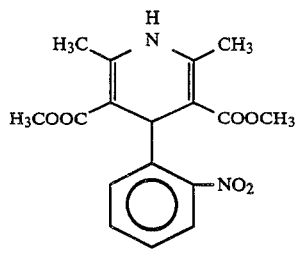

B.

which is disclosed in U.S. Pat. Nos. 3,644,627 and 3,485,847.

Other preferred 4-phenyl-1,4-dihydropyridine calcium antagonists suitable for use herein include niludipine, that is, the compound of formula A wherein $R_1$ is —$(CH_2)_2OC_3H_7$, $R_2$ is —$(CH_2)_2OC_3H_7$ and $NO_2$ is at the 3-position (disclosed in U.S. Pat. Nos. 3,488,359 and 3,574,843); nimodipine, that is the compound of formula A wherein $R_1$ is —$(CH_2)_2OCH_3$, $R_2$ is —$CH(CH_3)_2$ and $NO_2$ is at the 3-position (disclosed in U.S. Pat. Nos. 3,799,934 and 3,932,645); nitrendipine, that is, the compound of formula A wherein $R_1$ is —$CH_2CH_3$, $R_2$ is —$CH_3$ and $NO_2$ is at the 3-position (disclosed in U.S. Pat. Nos. 3,799,934 and 3,932,645); and nisoldipine, that is, the compound of formula A wherein $R_1$ is —$CH_3$, $R_2$ is —$CH_2CH(CH_3)_2$ and $NO_2$ is at the 2-position (disclosed in U.S. Pat. Nos. 3,799,934, 3,932,645 and 4,154,839).

Other calcium channel blockers which may be employed herein include the benzothiazepine derivatives disclosed in U.S. Pat. Nos. 4,654,335 and 4,584,131, benzodiazepine derivatives disclosed in U.S. Pat. Nos. 4,650,797 and 4,647,561, and pyrimidine derivatives such as disclosed in U.S. Pat. Nos. 4,684,656, 4,689,414 and 4,684,655.

A wide variety of other medicaments which are orally administered in tablet form can also be used in the form of beadlets prepared according to this invention. These include, for example, adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, curariform agents such as chlorisondamine and the like, tranquilizers and muscle relaxants such as fluphenazine, chlorpromazine, triflupromazine, mephenesin, meprobamate and the like, antidepressants like amitriptyline, nortriptyline, and the like, antihistamines such as diphenhydramine, dimenhydrinate, tripelennamine, perphenazine, chlorprophenazine, chlorprophenpyridamine, chlorpheniramine maleate, brompheniramine maleate, terfenadine and the like, hypotensive agents such as rauwolfia, reserpine, spironolactone, methyldopa, hydralazine HCl, clonidine HCl, prazosin HCl, amiloride HCl, and the like, cardioactive agents such as bendroflumethiazide, flumethiazide, chlorothiazide, hydrochlorothiazide, chlorothalidone, aminotrate, and procainamide, decongestants such as phenylpropanolamine HCl, pseudoephedrine and the like, antiinflammatory agents such as indomethacin, ibuprofen, naproxen, piroxicam and the like, renin inhibitors, bronchodialators such as theophylline, steroids such as testosterone, prednisolone, and the like, antibacterial agents, e.g., sulfonamides such as sulfadiazine, sulfamerazine, sulfamethazine, sulfisoxazole and the like, antimalarials such as chloroquine and the like, antibiotics such as the tetracyclines, nystatin, streptomycin, cephradine and other cephalosporins, penicillin, semi-synthetic penicillins, griseofulvin and the like, sedatives such as chloral hydrate, phenobarbital and other barbiturates, glutethimide, antitubercular agents such as isoniazid and the like, analgesics such as aspirin, acetaminophen, propoxyphene, meperidine and the like, vitamins, etc. These substances are frequently employed either as the free compound or in a salt form, e.g., acid addition salts, basic salts like alkali metal salts, etc. Other therapeutic agents having the same or different physiological activity can also be employed in pharmaceutical preparation within the scope of the present invention.

The disclosure of all of the above-mentioned U.S. patents are incorporated herein by reference.

The beadlets of the invention may contain one or combinations of two or more of the above pharmaceuticals. Particularly preferred are an ACE inhibitor alone such as captopril, a calcium channel blocker alone, such as diltiazem, nifedipine or verapamil, a combination of an ACE inhibitor and calcium channel blocker in a weight ratio to each other of within the range of from about 0.1:1 to about 10:1, such as a combination of captopril, enalapril, zofenopril, fosinopril or any of the other disclosed ACE inhibitors and diltiazem, captopril or any of the other disclosed ACE inhibitors and nifedipine; a combination of a beta blocker and calcium channel blocker in a weight ratio to each other of within the range of from about 0.1:1 to about 10:1, such as a combination of nadolol, propranolol, atenolol and the like with any of the calcium channel blockers disclosed herein; a combination of an ACE inhibitor as disclosed herein and a diuretic, such as hydrochlorothiazide, bendroflumethiazide, chlorthalidone and the like in a weight ratio to each other of within the range of from about 0.1:1 to about 10:1.

It will also be understood that beadlets containing one or more pharmaceuticals may be physically mixed with other beadlets containing one or more different pharmaceuticals in a single capsule shell or compressed into a tablet.

The organic carboxylic acid is essential for good beadlet formation via the extrusion-spheronization route in that it imparts plasticity to the wet mass and thus enables the formation of hard beadlets having a desired narrow particle size range of from about 0.8 to about 2 mm diameter. The organic acid will be present in the beadlet formulation in an amount within the range of from about 5 to about 50% by weight and preferably from about 10 to about 40% by weight.

Examples of organic carboxylic acids suitable for use herein include, but are not limited to, citric acid, malic acid, tartaric acid, uumaric acid, maleic acid and succinic acid, with citric acid being preferred.

The non-lipophilic binder-excipient will be present in an amount within the range of from about 3 to about 70% by weight of the beadlet and preferably from about 5 to about 60% by weight of the beadlet. Preferred binder-excipient for use in the beadlet of the invention will be microcrystalline cellulose. In such case the binder may serve as an excipient as well. However, other binders may be employed by themselves or together with known excipeints. Such binders may be hydrophilic polymers or hydrocolloids formed of water-swellable polymeric substances such as cellulosic polymers and gums. The hydrocolloid, where employed, will preferably comprise one or more cellulose polymers which are cellulose ethers such as methyl cellulose, cellulose alkyl hydroxylates such as hydroxypropylmethyl cellulose (low viscosity of 2 to 200 cp), hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose, or acrylic acid homo- or copolymers or alkali metal salts thereof.

It is to be understood that other known hydrocolloids may be employed in the present invention, including, for example, gelatin, polyvinylpyrrolidone, pectin, gum acacia, carrageenan, guar gum, gum tragacanth, gum xanthan, ammonium, alginic acid or sodium alginate or mixtures thereof. Other examples of suitable hydrocolloids are set out in U.S. Pat. No. 4,140,755 to Sheth et al.

The coating layer which may optionally be applied over the beadlet may comprise any conventional coating formulation and will include one or more film-formers or binders, such as a hydrophilic polymer like hydroxypropylmethyl cellulose and a hydrophobic polymer like ethyl cellulose, cellulose acetate, polyvinyl alcohol-maleic anhydride copolymers, acrylic acid polymers, such as acrylic acid-methacrylic acid ester copolymer, polyvinyl alcohols, β-pinene polymers, glyceryl esters of wood resins and the like, and one or more plasticizers, such as triethyl citrate, tributyl citrate, diethyl phthalate, acetylated monoglycerides, propylene glycol, glycerin, butyl phthlate, castor oil and the like. A preferred coating will comprise a sealcoat of hydroxypropyl methyl cellulose plasticized with polyethylene glycol followed by a rate controlling barrier coat of ethyl cellulose plasticized with acetylated monoglycerides (Myvacet 9-40).

The film formers are applied from a solvent system containing one or more solvents including water, alcohols like methyl alcoho, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent composition.

A preferred modified release beadlet in accordance with the present invention will include a core containing from about 5 to about 40% by weight ACE inhibitor such as captopril, alone, or from about 10 to about 50% by weight diltiazem or nifedipine, alone, or combinations of captopril with diltiazem or nifedipine, in amounts mentioned above, from about 15 to about 60% by weight of the binder which preferably is microcrystalline cellulose and optionally from about 3 to about 10% by weight of hydroxypropylmethyl cellulose, from about 10 to about 35% by weight of organic acid which preferably is citric acid (all of such % being based on the weight of the core), and an optional coating which contains one or more film formers such as from about 20 to about 75% by weight hydroxypropyl methyl cellulose, from about 5 to about 60% by weight ethyl cellulose and one or more plasticizers such as from about 5 to about 25% by weight polyethylene glycol and from about 5 to about 40% by weight acetylated monoglycerides, all % being based on the total weight of the coating.

Optional inert fillers which may be present include lactose, sucrose, mannitol, xylitol and the like.

It will be appreciated that in accordance with the present invention, regardless of whether optional ingredients are present, the % by weight of organic acid present (from 5 to 50%) as described above will be maintained to achieve formation of hard beadlets having a narrow particle size distribution.

In forming the beadlets in accordance with the method of the invention, the medicament or combination of medicaments, organic carboxylic acid, such as citric acid, and binder-excipients are thoroughly mixed and kneaded with water, for example, using a conventional blender to form a wet mass. Thereafter, the wet mass is extruded, for example, employing a Nica, Luwa or other type extruder to form an extrudate which is then passed through spheronizing equipment, such as Nica, Luwa or other type, which convert the extrudate into beadlets of appropriate particle size range. The beadlets may then be dried by tray drying oven or fluid bed drying. If desired, the beadlets may be coated, for example, with a solution or dispersion of film former and plasticizer by pan coating, fluid bed coating and the like.

The so-formed beadlets may be filled into hard shell capsules or compressed into a tablet to provide formulations administered in single or divided doses of from about 2 to 200 mg, preferably from about 5 to about 150 mg/one to four times daily.

The following Examples represent preferred embodiments of the present invention. Unless otherwise indicated, all temperatures are expressed in degrees Centigrade.

EXAMPLE 1

A modified release beadlet formulation capable of slowly releasing the angiotensin converting enzyme inhibitor captopril over a period of up to 6 hours and having the following composition was prepared as described below.

| Ingredient | Amount in Parts by Weight |
| --- | --- |
| Captopril | 27 |
| Citric acid | 30 |
| Microcrystalline cellulose* | 43 |

*amount may vary to reflect chemical purity of captopril

The above ingredients were mixed and kneaded using water in a planetary mixer to form a wet mass. The wet mass was passed through a Nica E140 extruder to form an extrudate (~1 mm diameter). The extrudate was then passed through a Nica spheronizer to form beadlets. The beadlets were then dried at 40° C. for 12–18 hours in a tray drying oven or for 2–4 hours in a fluid bed dryer. A fraction of the so-formed beadlets were filled into hard shell pharmaceutical capsules to form one of the formulations of the invention.

EXAMPLE 2

A modified release coated-beadlet formulation having the following composition was prepared as follows.

| Ingredient | | mg/Dose |
| --- | --- | --- |
| (i) Core | | |
| Captopril | | 100 |
| Microcrystalline cellulose | | 159.1 |
| Citric acid | | 37. |
| Lactose | | 74.1 |
| (ii) Sealcoat | | |
| Hydroxypropyl methyl cellulose | ca. | 8.3 |
| Polyethylene glycol | ca. | 2.8 |
| (iii) Barriercoat | | |
| Ethyl cellulose (as Aquacoat ® solids) | ca. | 4.2 |
| Acetylated monoglycerides (Myvacet ®9-40) | ca. | 1.3 |

The beadlet cores were prepared as described in Example 1. After the dried beadlets were formed, they were coated via a two step process as follows. An aqueous solution of hydroxypropyl methyl cellulose (7.5% by weight) and polyethylene glycol (2.5% by weight) was prepared and sprayed on to the beadlets to form a sealcoat. The beadlets were then coated with a barriercoat using a commercially available aqueous dispersion of ethyl cellulose (e.g., Aquacoat ®) (30% by weight) mixed with acetylated monoglycerides (9.5% by weight). The beadlets were then filled into hard shell pharmaceutical capsules.

EXAMPLE 3

A modified release coated-beadlet formulation having the following composition was prepared as follows.

| Ingredient | | % by Weight of Coated Beadlet |
| --- | --- | --- |
| Core | | |
| Captopril | | 26.2 |
| Citric acid | | 29.1 |
| Microcrystalline cellulose | | 41.8 |
| Film coating | | |
| Ethyl cellulose | ca. | 2.6 |
| Triethyl citrate | ca. | 0.3 |

The beadlet cores were prepared as described in Example 1.

Ethyl cellulose (9 parts) and triethylcitrate (1 part) were dissolved in ethyl alcohol (90 parts) and then sprayed on to the beadlets to form coated product. The so-formed beadlets were then filled into hard shell pharmaceutical capsules.

EXAMPLES 4 to 8

Following the procedure of Examples 1 to 3 except substituting the following ACE inhibitor, organic acid and binder-excipients, the following beadlet compositions may be prepared.

| Ex. No. | ACE Inhibitor | Organic acid | Binder |
|---|---|---|---|
| 4. | N—(1-ethoxycarbonyl-3-phenylpropyl)-L-proline | Citric acid | Microcrystalline cellulose |
| 5. | (S)—1-[6-Amino-2-[[hydroxy(4-phenyl-butyl)phosphinyl]-oxy]-1-oxohexyl]-L-proline | Malic acid | Microcrystalline cellulose and hydroxypropyl methyl cellulose |
| 6. | Lisinopril | Tartaric acid | Na carboxymethyl cellulose |
| 7. | Zofenopril | Succinic acid | Gelatin, pectin and Na carboxymethyl cellulose |
| 8. | Fosinopril | Maleic acid | Microcrystalline cellulose |

EXAMPLE 9

A beadlet formulation is prepared as described in Example 1 except that 20 parts of diltiazem are employed in place of the 27 parts of captopril.

EXAMPLE 10

Captopril beadlets are prepared as described in Example 2 and diltiazem beadlets are prepared as described in Example 2 (except that 25 parts of diltiazem are employed) and equal amounts of such beadlets are filled into hard gelatin capsules.

EXAMPLE 11

A beadlet formulation is prepared as described in Example 2 except that 12 parts of captopril and 10 parts of nifedipine or 10 parts of diltiazem are employed in place of the 27 parts of captopril.

EXAMPLE 12

A beadlet formulation is prepared as described in Example 1 except that 27 parts of nadolol are employed in place of the 27 parts of captopril.

EXAMPLE 13

A beadlet formulation is prepared as described in Example 1 except that 13.5 parts of nadolol and 13.5 parts of nifedipine are employed in place of 27 parts of captopril.

It will be appreciated that the beadlet formulations of the invention prepared in Examples 1 to 13 may be filled into capsules or compressed into tablets employing conventional pharmaceutical techniques.

What is claimed is:

1. A modified release formulation in the form of an extruded-spheronized beadlet from which medicament is released at a controlled rate, said beadlet comprising a medicament, an organic carboxylic acid to facilitate spheronization, to impart hardness to the beadlet and aid in obtaining a desired narrow particle size distribution of beadlets, and a non-lipophilic non-fat binder, said medicament being present in a weight percent of from about 3 to about 60%, and said organic carboxylic acid being present in an amount within the range of from about 5 to about 50% by weight of said beadlet, said beadlet having a hardness of at least about 2 Strong-Cobb units.

2. The formulation as defined in claim 1 wherein the organic carboxylic acid is citric acid, malic acid, tartaric acid, maleic acid, fumaric acid or succinic acid.

3. The formulation as defined in claim 2 wherein the organic carboxylic acid is citric acid.

4. The formulation as defined in claim 1 wherein said medicament is an angiotensin converting enzyme (ACE) inhibitor.

5. The formulation as defined in claim 4 wherein said ACE inhibitor is selected from the group consisting of a substituted proline derivative, an ether or thioether mercaptoacyl proline, a carboxyalkyl dipeptide derivative, a phosphinylalkanoyl proline derivative, a phosphonamidate derivative, a phosphonate derivative and a prolylamino acid derivative.

6. The formulation as defined in claim 4 wherein said ACE inhibitor is captopril.

7. The formulation as defined in claim 5 wherein said ACE inhibitor is zofenopril or fosinopril.

8. The formulation as defined in claim 5 wherein said ACE inhibitor is enalapril.

9. The formulation as defined in claim 1 wherein said binder is microcrystalline cellulose.

10. The formulation as defined in claim 1 wherein said binder is a hydrocolloid.

11. The formulation as defined in claim 10 wherein said hydrocolloid is a cellulose ether.

12. The formulation as defined in claim 11 wherein said cellulose ether is hydropropylmethyl cellulose.

13. The formulation as defined in claim 1 wherein said medicament is captopril, said organic carboxylic acid is citric acid and said binder is microcrystalline cellulose.

14. The formulation as defined in claim 13 wherein said captopril is present in an amount within the range of from about 5 to about 40% by weight and said citric acid is present in an amount within the range of from about 10 to about 35% by weight.

15. The formulation as defined in claim 1 including a film-coating on said beadlets.

16. The formulation as defined in claim 1 wherein said medicament is a beta blocker alone or in combination with a calcium channel blocker.

17. The formulation as defined in claim 16 wherein said beta blocker is nadolol, propranol or atenolol and said calcium channel blocker is diltiazem, nifedipine, verapamil or tiapamil.

18. The formulation as defined in claim 1 wherein said medicament is a calcium channel blocker alone or in combination with an ACE inhibitor.

19. The formulation as defined in claim 1 wherein said calcium channel blocker is diltiazem, nifedipine or verapamil and said ACE inhibitor is captopril, enalapril, zofenopril or fosinopril.

20. The formulation as defined in claim 19 wherein the medicament is a combination of captopril and diltiazem.

21. The formulation as defined in claim 1 wherein said medicament is a combination of an ACE inhibitor and a diuretic.

22. The formulation as defined in claim 21 wherein said ACE inhibitor is captopril, enalapril, zofenopril or fosinopril and said diuretic is hydrochlorothiazide.

23. The formulation as defined in claim 1 including two or more medicaments in each beadlet.

24. The formulation as defined in claim 1 including a mixture of beadlets, each beadlet containing at least one medicament which may be the same or different from medicament contained in another beadlet.

25. The formulation as defined in claim 1 comprising a plurality of beadlets contained within a capsule.

26. The formulation as defined in claim 1 compressed into a tablet.

27. A method for preparing beadlets containing medicament, which comprises forming a wet mass of medicament an organic carboxylic acid and binder, said organic carboxylic acid imparting needed plasticity to the wet mass thereby reducing water requirements and shortening procesing time, extruding said wet mass to form an extrudate, forming extrudate into beadlets having an average size distribution of within the range of from about 0.8 to about 2 mm diameter, and drying said beadlets, said beadlets having a hardness of at least about 2 Strong-Cobb units.

28. The method as defined in claim 27 wherein said medicament is an ACE inhibitor alone or in combination with a calcium channel blocker.

29. The method as defined in claim 27 wherein said ACE inhibitor is captopril and said binder is microcrystalline cellulose.

30. The method as defined in claim 27 wherein said organic carboxylic acid is citric acid, malic acid, fumaric acid, tartaric acid, maleic acid or succinic acid.

31. The method as defined in claim 30 wherein the organic carboxylic acid is citric acid.

32. The method as defined in claim 27 further including the step of applying a film coating on the dried beadlets.

33. A method of alleviating hypertension in a mammalian specie which comprises administering to a mammalian specie in need of such treatment the sustained release tablet as defined in claim 1 containing an effective amount of a beta blocker or an angiotensin converting enzyme inhibitor each alone or each in combination with a calcium antagonist.

34. The method as defined in claim 33 wherein said ACE inhibitor is captopril, said beta blocker is nadolol or propranolol and said calcium antagonist is diltiazem or nifedipine.

35. A modified release formulation in the form of an extruded-spheronized beadlet from which medicament is released at a controlled rate, said beadlet comprising a medicament, an organic carboxylic acid to facilitate spheroidization, to impart hardness to the beadlet and aid in obtaining a desired narrow particle size distribution of beadlets, and a non-lipophilic non-fat binder, said medicament being present in a weight percent of from about 3 to about 60%, and said organic carboxylic acid being present in an amount within the range of from about 5 to about 50% by weight of said beadlet, said beadlet prepared by the method of extruding a wet mass of the above ingredients to form an extrudate and spheronizing the extrudage to form beadlets.

* * * * *

REEXAMINATION CERTIFICATE (1554th)

United States Patent [19]

Joshi et al.

[11] B1 4,808,413

[45] Certificate Issued Sep. 10, 1991

[54] PHARMACEUTICAL COMPOSITIONS IN THE FORM OF BEADLETS AND METHOD

[75] Inventors: Yatindra M. Joshi, Piscataway; William R. Bachman, North Brunswick; Nemichand B. Jain, Monmouth Junction, all of N.J.

[73] Assignee: E. R. Squibb & Sons, Inc., Princeton, N.J.

Reexamination Request:
No. 90/002,213, Nov. 28, 1990

Reexamination Certificate for:
Patent No.: 4,808,413
Issued: Feb. 28, 1989
Appl. No.: 140,281
Filed: Dec. 31, 1987

Related U.S. Application Data

[63] Continuation-in-part of Ser. No. 43,584, Apr. 28, 1987, abandoned.

[51] Int. Cl.$^5$ .................... A61K 9/14; A61K 9/26; A61K 9/52
[52] U.S. Cl. .................... 424/458; 424/469; 424/489; 424/499
[58] Field of Search ............. 424/458, 469, 489, 499

[56] References Cited

U.S. PATENT DOCUMENTS

4,728,512  3/1988  Mehta et al. .................... 424/458
4,795,001  12/1988  Mehta et al. .................... 424/458

OTHER PUBLICATIONS

Hu, Ming et al, *Passive and Carrier–Mediated Intestinal Absorption Components of Captopril*, College of Pharmacy, Univ. of Mich., pp. 1007–1011, Aug. 4, 1988.

*Primary Examiner*—Michael Lusignan

[57] ABSTRACT

A pharmaceutical composition is provided which is in the form of a plurality of beadlets, adapted to be filled into pharmaceutical hard shell capsules, or compressed into tablets, which beadlets are formed of a pharmaceutical such as an ACE inhibitor, for example, captopril, a beta-blocker such as nadolol, propranolol or atenolol, a calcium channel blocker such as diltiazem or nifedipine or other pharmaceuticals including combinations thereof, binder such as microcrystalline cellulose, and at least 5% by weight of an acid processing aid, such as citric acid, which imparts plasticity to the wet mass needed for efficient extrusion and spheronization. A method for forming beadlets is also provided which includes the steps of extruding a composition as described above, and subjecting the resulting extrudate to a spheronization step wherein an acid processing aid such as citric acid is employed to improve processing and form improved beadlets.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4–8, 16, 17 are cancelled.

Claims 1, 13, 18, 19, 21, 22, 27–29, 33–35 are determined to be patentable as amended.

Claims 2, 3, 9–12, 14, 15, 20, 23–26, 30–32, dependent on an amended claim, are determined to be patentable.

1. A modified release formulation in the form of an extruded-spheronized beadlet from which medicament is released at a controlled rate, said beadlet comprising a medicament *which is captopril*, an organic carboxylic acid to facilitate spheronization, to impart hardness to the beadlet and aid in obtaining a desired narrow particle size distribution of beadlets, and a non-lipophilic non-fat binder, said medicament being present in a weight percent of from about 3 to about 60%, and said organic carboxylic acid being present in an amount within the range of from about 5 to about 50% by weight of said beadlet, said beadlet having a hardness of at least about 2 Strong-Cobb units.

13. The formulation as defined in claim 1 wherein [said medicament is captopril,] said organic carboxylic acid is citric acid and said binder is microcrystalline cellulose.

18. The formulation as defined in claim 1 wherein said medicament is a calcium channel blocker [alone or] in combination with [an ACE inhibitor] *captopril*.

19. The formulation as defined in claim 1 wherein said calcium channel blocker is diltiazem, nifedipine or verapamil [and said ACE inhibitor is captopril, enalapril, zofenopril or fosinopril].

21. The formulation as defined in claim 1 wherein said medicament is a combination of [an ACE inhibitor] *captopril* and a diuretic.

22. The formulation as defined in claim 21 wherein [said ACE inhibitor is captopril, enalapril, zofenopril or fosinopril and] said diuretic is hydrochlorothiazide.

27. A method for preparing beadlets containing medicament, which comprises forming a wet mass of medicament *which is captopril*, an organic carboxylic acid and binder, said organic carboxylic acid imparting needed plasticity to the wet mass thereby reducing water requirements and shortening [procesing] *processing* time, extruding said wet mass to form an extrudate, forming extrudate into beadlets having an average size distribution of within the range of from about 0.8 to about 2 mm diameter, and drying said beadlets, said beadlets having a hardness of at least about 2 Strong-Cobb units.

28. The method as defined in claim 27 wherein said medicament is [an ACE inhibitor] *captopril* alone or in combination with a calcium channel blocker.

29. The method as defined in claim 27 wherein said [ACE inhibitor is captopril and said] binder is microcrystalline cellulose.

33. A method of alleviating hypertension in a mammalian specie which comprises administering to a mammalian specie in need of such treatment the sustained release tablet as defined in claim 1 containing an effective amount of [a beta blocker or] *captopril as* an angiotensin converting enzyme inhibitor [each] alone or [each] in combination with a calcium antagonist.

34. The method as defined in claim 33 wherein [said ACE inhibitor is captopril, said beta blocker is nadolol or propranolol and] said calcium antagonist is diltiazem or nifedipine.

35. A modified release formulation in the form of an extruded-spheronized beadlet from which medicament is released at a controlled rate, said beadlet comprising a medicament *which is captopril*, an organic carboxylic acid to facilitate spheroidization, to impart hardness to the beadlet and aid in obtaining a desired narrow particle size distribution of beadlets, and a non-lipophilic non-fat binder, said medicament being present in a weight percent of from about 3 to about 60%, and said organic carboxylic acid being present in an amount within the range of from about 5 to about 50% by weight of said beadlet, said beadlet prepared by the method of extruding a wet mass of the above ingredients to form an extrudate and spheronizing the [extrudage] *extrudate* to form beadlets.

* * * * *